(12) United States Patent
Hohmann et al.

(10) Patent No.: US 8,552,858 B2
(45) Date of Patent: Oct. 8, 2013

(54) SIMULATION AND VISUALIZATION OF SCATTERED RADIATION

(75) Inventors: Steffen Gunther Hohmann, Köln (DE); Christian Baeumer, Hargenrath (BE); Joerg Bredno, San Francisco, CA (US); Norbert Conrads, Raeren (BE); Olivier Ecabert, Aachen (DE); Klaus Juergen Engel, Aachen (DE); Christoph Herrmann, Aachen (DE); Rainer Kiewitt, Roetgen (DE); Helko Lehmann, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 918 days.

(21) Appl. No.: 12/527,930

(22) PCT Filed: Feb. 22, 2008

(86) PCT No.: PCT/IB2008/050655
§ 371 (c)(1),
(2), (4) Date: Feb. 4, 2010

(87) PCT Pub. No.: WO2008/104915
PCT Pub. Date: Sep. 4, 2008

(65) Prior Publication Data
US 2010/0127859 A1    May 27, 2010

(30) Foreign Application Priority Data

Feb. 27, 2007  (EP) .................................... 07103144

(51) Int. Cl.
*G08B 21/00*  (2006.01)
*G01N 21/47* (2006.01)
*G01N 23/04* (2006.01)
*F21V 33/00* (2006.01)
*A61B 6/08* (2006.01)
*A61B 6/00* (2006.01)
*A61B 6/04* (2006.01)
*A61B 5/05* (2006.01)

(52) U.S. Cl.
USPC ................ 340/540; 378/7; 378/57; 378/206; 600/407

(58) Field of Classification Search
None
See application file for complete search history.

(56) References Cited

U.S. PATENT DOCUMENTS

| 4,277,686 | A | 7/1981 | Harding |
| 4,423,522 | A | 12/1983 | Harding |
| 5,270,925 | A * | 12/1993 | Stegehuis ........................ 378/7 |
| 5,537,453 | A * | 7/1996 | Williams et al. .............. 378/206 |
| 5,647,663 | A | 7/1997 | Holmes |
| 6,422,751 | B1 | 7/2002 | Aufrichtig et al. |
| 6,639,964 | B2 * | 10/2003 | Schneider et al. ................ 378/7 |

(Continued)

FOREIGN PATENT DOCUMENTS

WO    2004066215 A1    8/2004

*Primary Examiner* — George Bugg
*Assistant Examiner* — Renee Dorsey

(57) ABSTRACT

Scattered radiation has non-intuitive properties. A signalling system (28) is presented which provides a perceptible signal (34) being indicative of a predicted or measured spatial distribution of scattered radiation. An embodiment provides for easy assessment of the individual risk of scattered radiation exposure for personnel working in an environment exposed to scattered radiation. A method for predicting a distribution of scattered radiation takes into account at least one object related parameter (18) and at least one radiation related parameter (22) and, in response hereto, predicts a distribution of scattered radiation.

21 Claims, 8 Drawing Sheets

(56) References Cited

U.S. PATENT DOCUMENTS

| | | |
|---|---|---|
| 6,957,096 B2 * | 10/2005 | Sfez et al. .................. 600/407 |
| 6,983,230 B2 | 1/2006 | Baroudi |
| 7,091,508 B2 | 8/2006 | Goldstein |
| 7,092,482 B2 * | 8/2006 | Besson ......................... 378/37 |
| 7,110,495 B2 | 9/2006 | Tamegai |
| 7,119,903 B1 * | 10/2006 | Jones .......................... 356/446 |
| 7,281,811 B2 * | 10/2007 | Thuot Rann et al. .......... 362/96 |
| 7,471,759 B2 * | 12/2008 | Rinkel et al. .................... 378/7 |
| 2007/0071169 A1 | 3/2007 | Yeo et al. |

* cited by examiner

SIMULATION AND VISUALIZATION OF SCATTERED RADIATION

FIELD OF THE INVENTION

The invention relates to the field of environments where individuals are exposed to scattered radiation.

BACKGROUND OF THE INVENTION

U.S. Pat. No. 6,983,230 B2 discloses a method and an apparatus for determining a radiation dosage received by a product being exposed to radiation in an irradiator cell through a computer simulation. The method initiates with a point on the product being defined. Then, pre-calculated lengths between the point on the product and the radiation source at each of a set of locations in the cell are identified. Next, a dosage of radiation to be received by the point on the product at each location is calculated using the pre-calculated lengths.

SUMMARY OF THE INVENTION

Scattered radiation which is generated upon irradiation of an object with radiation has non-intuitive properties. An example of such a radiation is X-ray radiation. It would be advantageous to provide a method or an apparatus which can contribute to improve the awareness of scattered radiation of personnel working in a surrounding of a device which involves radiation.

To better address this concern, in a first aspect of the invention a signalling system is presented which comprises a control unit for providing control signals in response to a predicted or measured spatial distribution of scattered radiation. The signalling system further comprises a signalling unit for providing at least one perceptible signal in response to the control signals, the at least one perceptible signal being indicative of the predicted or measured spatial distribution of scattered radiation. An advantage of this system is that personnel is made aware of scattered radiation.

Further according to the first aspect of the invention a signalling method is presented which comprises providing at least one perceptible signal indicative of a predicted or measured spatial distribution of scattered radiation.

According to an embodiment of the invention, a signalling system is presented wherein the signalling unit comprises a display device for displaying at least one of the at least one perceptible signal. An advantage of this embodiment is flexibility, since the content displayed by a display device can easily be changed.

According to another embodiment of the invention, a signalling system is presented, wherein at least one of the at least one perceptible signal is a light pattern on a floor and the signalling unit comprises at least one light source for generating the light pattern. An advantage of this embodiment is that the light pattern is indicative of the spatial distribution of radiation. A further advantage of this embodiment is that the personnel only has to look at the floor region where she or he desires to go in order to get at least some qualitative information about the radiation dose in this region. Further, this embodiment can be advantageously used to provide a clear visibility of regions which correspond to a certain distribution of scattered radiation, e.g. in which the radiation dose is higher than in other regions. The light pattern on the floor can be realized by any appropriate method, e.g. by light sources located at the floor or by one or more image projectors which are located at one or more of a wall, a ceiling, a technical equipment, etc.

According to still another embodiment of the invention, a signalling system is presented wherein one or more predetermined intensity intervals are defined, wherein providing at least one perceptible signal indicative of the predicted or measured spatial distribution of scattered radiation includes illuminating portions of the floor, the portions being vertical projections of boundaries of spatial regions in which the radiation intensity is within one of the one or more predetermined radiation intensity intervals. An advantage of this embodiment is that the illuminated portions thereby generate iso-risk lines on the floor like height lines known from cartographic maps.

According to still another embodiment of the invention, a signalling system is presented wherein one or more intensity intervals are defined. In this embodiment, providing at least one perceptible signal indicative of the predicted or measured spatial distribution of scattered radiation includes illuminating portions of the floor, the portions being projections of spatial regions in which the radiation intensity is within a predetermined radiation intensity interval. A specific color is associated with each of the radiation intensity intervals and each of the illuminated portions is illuminated with an illumination color corresponding to the respective radiation intensity interval. An advantage of this embodiment is that the possibility is provided to mark regions of high dose rates with a certain color which indicates to the personnel that the dose rate in the respective region is above a predetermined dose rate of the lower boundary of the intensity interval.

According to still another embodiment of the invention, a signalling system is presented wherein one or more radiation intensity intervals are defined, wherein providing at least one perceptible signal indicative of the predicted or measured spatial distribution of scattered radiation includes illuminating portions of the floor, the portions being projections of spatial regions in which the radiation intensity is within a predetermined radiation intensity interval. Further according to this embodiment, a specific illumination intensity is associated with each of the radiation intensity intervals. Further, each of the illuminated portions is illuminated with an illumination intensity corresponding to its respective radiation intensity interval.

According to still another embodiment of the invention, a signalling system is presented wherein at least one of the at least one perceptible signal is a light pattern on a surface of at least one object and wherein the signalling unit comprises at least one light source for generating the light pattern on the surface of the at least one object. Examples of such objects on which the light patterns are generated comprise e.g. technical equipment and personnel, e.g. clothes of the personnel. This embodiment can be employed to advantage e.g. in that any object or even the personnel itself can provide information on regions of different radiation dose rates.

According to still another embodiment of the invention, a signalling system is presented which further comprises a sensing device for sensing a position of an individual and providing a position signal to the control unit in response hereto. At least one of the at least one perceptible signal is an acoustic signal indicative of the predicted or measured spatial distribution of scattered radiation. The signalling unit further comprises at least one acoustic signal source for providing the acoustic signal in response to control signals of the control unit. In response to the predicted or measured spatial distribution of scattered radiation and the position signal, the control unit provides control signals to the at least one acoustic signal source. This embodiment can be employed to advantage e.g. in that a signal indicative of a spatial distribution of scattered radiation can be made perceptible to personnel without requiring the personnel to look at a visible signal.

According to still another embodiment of the invention, a signalling system according to any one of the above mentioned aspects or embodiments of the invention is presented, the signalling system further comprising a sensing device for sensing a position of an individual and providing a position signal to the control unit in response hereto. In this embodiment, at least one of the at least one perceptible signal is an acoustic signal indicative of the predicted or measured spatial distribution of scattered radiation at the position of the individual. Further, the signalling unit comprises an acoustic signal source for providing the acoustic signal in response to control signals of the control unit and said control unit is provided for providing said control signals to said acoustic signal source in response to said predicted or measured spatial distribution of scattered radiation and said position signal. An advantage of this embodiment is that the personnel can be acoustically warned of regions of a certain scattered radiation distribution, without requiring the personnel to look at a visible signal. In such an embodiment, the control unit may be provided for generating the control signals so as to vary a tone pitch of said acoustic signal in response to an intensity of said sensed radiation.

According to still another embodiment of the invention, a signalling system is presented, the signalling system comprising a radiation sensor for sensing radiation indicative of the spatial distribution of scattered radiation. The control unit is provided for providing the control signals in response to the sensed radiation. According to one embodiment of the invention, the radiation indicative of the spatial distribution of scattered radiation may be the spatial distribution of radiation itself, i.e the radiation sensor would be e.g. an X-ray sensor. According to still another embodiment of the invention, the radiation sensor may be a sensor for visible light. In this case, the radiation sensor may be provided for sensing light of a visible perceptible signal provided in response to the control signals of the signalling system. A radiation sensor may be advantageously employed in a wearable signalling system attached to a clothing of an individual working in an environment of scattered radiation. For example, an X-ray sensor for directly sensing scattered radiation may be positioned near the loin or the thorax of a personnel.

According to a second aspect of the invention, a method for predicting a spatial distribution of scattered radiation is presented which comprises the steps: 1. Providing at least one object related parameter which is related to an object that is subjected to a radiation. 2. Providing at least one radiation related parameter which is related to the radiation. 3. Predicting a spatial distribution of scattered radiation, which is generated by scattering of the radiation, in a surrounding of the object by taking into account the at least one object related parameter and the at least one radiation related parameter. The method can contribute to improve the awareness of scattered radiation of personnel working in a surrounding of a device which involves radiation since the information about the radiation dose rate of scattered radiation in a surrounding of a device which involves radiation is predicted and is therefore available before an irradiation of the surrounding of the radiation involving device takes place.

According to still another embodiment of the invention, a method is presented wherein at least one of the at least one object related parameter is a parameter of an algorithmic representation of the object. An advantage of this embodiment is that an algorithmic representation of the object can provide a good estimation on the distribution of radiation exposed scattering matter with very few object related parameters.

According to still another embodiment of the invention, a method is presented wherein the step of providing at least one object related parameter comprises acquiring an image of at least a part of the object and providing at least one of the at least one object related parameter in response to the image. An advantage of this embodiment is that an image may provide detailed information about the object subjected to the radiation.

According to still another embodiment of the invention, a method is presented wherein a surface portion of the object is illuminated with structured light and the image is an image of the surface portion of the object. An advantage of this embodiment is that a contour of the object can be imaged more easily.

According to still another embodiment of the invention, a method is presented wherein the distribution of scattered radiation is predicted by using Monte-Carlo simulation of the scattering of the radiation. An advantage of this embodiment is that Monte-Carlo simulations can provide a detailed prediction that can take into account all possible radiation interactions with geometries of arbitrary detail level.

According to still another embodiment of the invention, a method is presented wherein the distribution of scattered radiation is predicted by a superposition of pre-calculated Monte-Carlo results. An advantage of this embodiment is that by using pre-calculated results, the prediction of the radiation dose rate distribution for one configuration requires less time.

According to still another embodiment of the invention, a method is presented wherein predicting a distribution of scattered radiation further includes taking into account a measured spatial distribution of scattered radiation. An advantage of this embodiment is that the prediction of a spatial distribution of scattered radiation can be more refined. Further, the predicted spatial distribution can be verified at the locations of measurement of scattered radiation.

According to still another embodiment of the invention, a method is presented wherein the object is at least a part of a human body. The above mentioned methods can be used to advantage for predicting a spatial distribution of scattered radiation which is scattered by a human body or a part thereof.

According to still another embodiment of the invention, a method of operating a scatter prediction device is presented, the method comprising the steps of: A) Predicting a spatial distribution of scattered radiation by any one of the above mentioned aspects and embodiments. B) In response hereto providing at least one perceptible signal, the at least one perceptible signal being indicative of the predicted spatial distribution of scattered radiation.

According to still other embodiments of the invention, for each of the above mentioned methods according to aspects and embodiments of the invention, a computer program product is presented which enables a processor to carry out the respective one or several of the above mentioned methods.

According to still other embodiments of the invention, a scatter prediction device is presented, the device comprising a prediction unit for carrying out a method for predicting a spatial distribution of scattered radiation according to any one of the aspects and embodiments described herein, in order to provide the predicted spatial distribution of scattered radiation.

According to still another embodiment of the invention, the scatter prediction device further comprises a signalling system according to any one of the aspects and embodiments described herein.

An advantage of these embodiments is that the awareness of a scattered radiation may be improved.

The above mentioned devices and methods according to aspects and embodiments of the invention are well suited for use with X-rays as the radiation. In particular, the above mentioned devices and methods according to aspects and embodiments of the invention are well suited for use in an intervention room for performing interventions under X-ray surveillance, e.g. for use in a catheter laboratory (=Cathlab). According to still another embodiment of the invention, an intervention room for performing interventions under X-ray surveillance is presented, the intervention room comprising a signalling system according to any one of the aspects and embodiments presented herein. According to still another embodiment of the invention, an intervention room for performing interventions under X-ray surveillance is presented, the intervention room comprising any one of the scatter prediction devices discussed above.

At least part of the above mentioned devices and methods according to aspects and embodiments of the invention are well suited for use with a mobile X-ray examination device. According to still another embodiment of the invention, a mobile X-ray examination device is presented, the mobile X-ray examination device comprising a signalling system according to any one of the aspects and embodiments of a signalling system discussed herein. According to still another embodiment of the invention, a mobile X-ray examination device is presented, the mobile X-ray examination device comprising a scattering prediction device according to any one of the aspects and embodiments of a scatter prediction device discussed herein.

Generally, the term "providing at least one perceptible signal being indicative of the predicted spatial distribution of scattered radiation" includes "making regions of different dose rates perceptible, wherein said regions of different dose rates are indicative of the predicted spatial distribution of scattered radiation". In any aspect or embodiment, a signalling system may be employed which makes at least one region corresponding to a certain dose rate of scattered radiation perceptible in response to the control signals of the control unit of the signalling system.

In summary, scattered radiation has non-intuitive properties. A signalling system is presented which provides a perceptible signal being indicative of a predicted spatial distribution of scattered radiation. An embodiment provides for easy assessment of the individual risk of scattered radiation exposure for personnel working in an environment exposed to scattered radiation. A method for predicting a distribution of scattered radiation takes into account at least one object related parameter and at least one radiation related parameter and, in response hereto, predicts a distribution of scattered radiation.

These and other aspects of the invention will be apparent from and elucidated with reference to the embodiments described hereinafter.

BRIEF DESCRIPTION OF THE DRAWINGS

In the following detailed description, reference is made to the drawings in which.

DETAILED DESCRIPTION OF EMBODIMENTS

Figure 1:
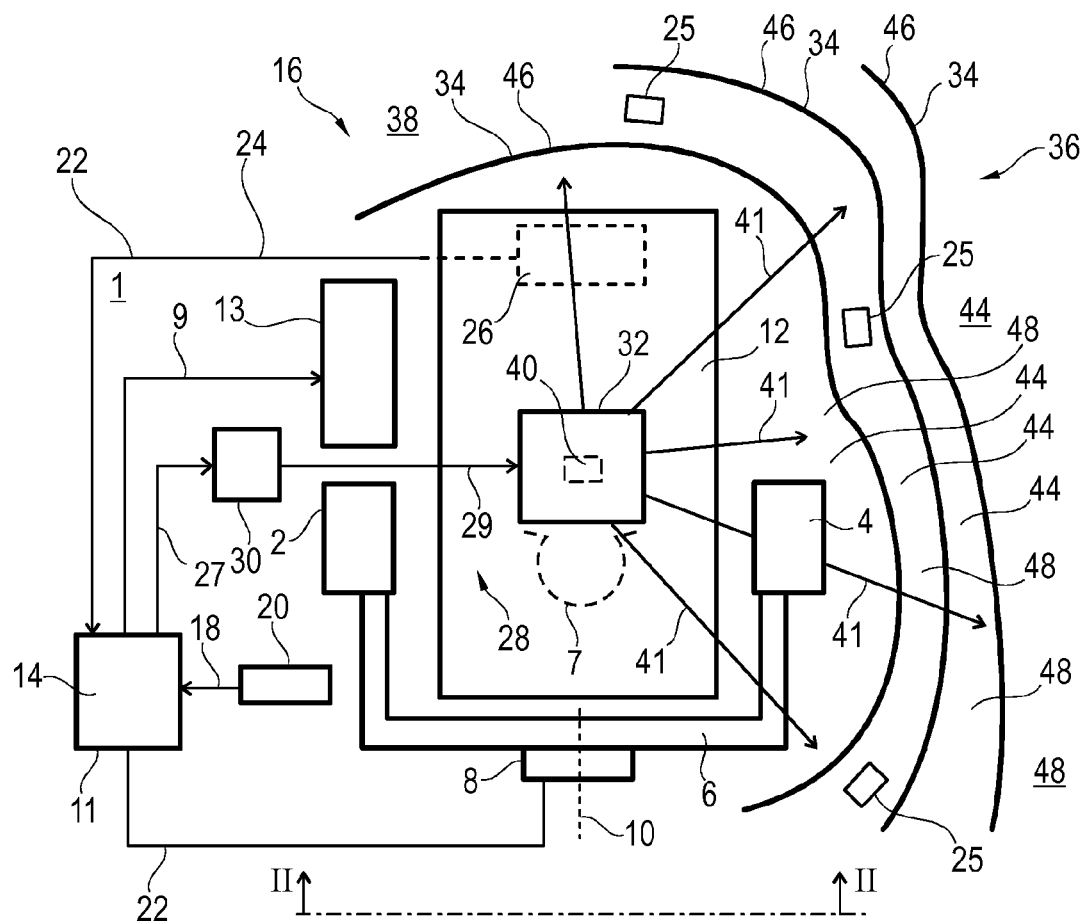
FIG. 1 shows a schematic top view of an embodiment of a scatter prediction device according to the invention.
Figure 2:
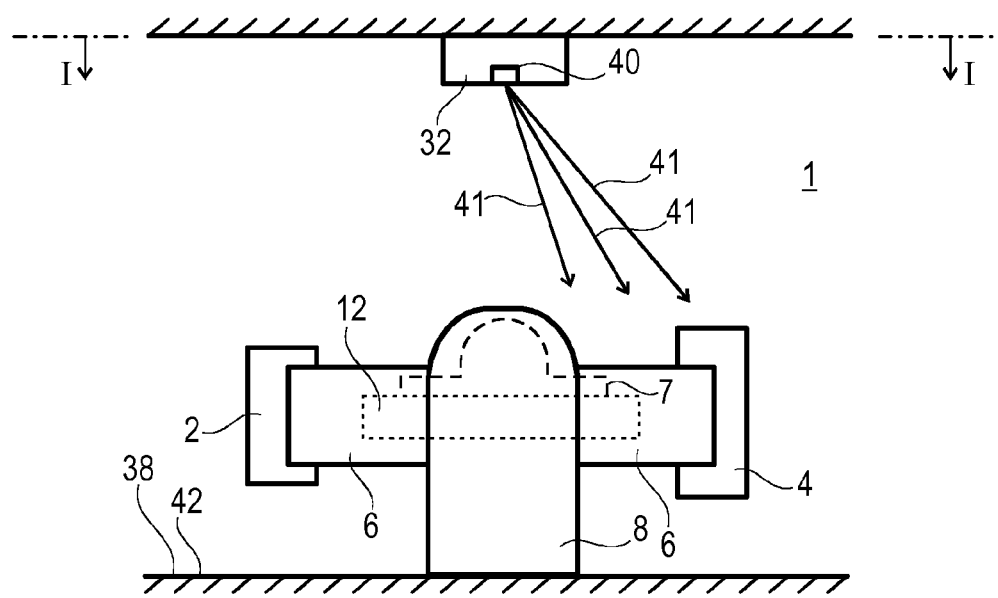
FIG. 2 shows a front view of the scatter prediction device of FIG. 1.

With reference to the drawings, illustrative embodiments of the present invention will now be described in more detail.

In the following, the principles and some exemplary embodiments of the invention will be described for examples, where an object, e.g. a human body or part of a human body is irradiated with X-ray radiation. However, it should be understood that these embodiment is arbitrarily selected for illustrative purposes.

Interventional radiologists are exposed to scattered x-ray radiation during their daily work in the catheter laboratory (Cathlab). Installed and individual dose protection equipment and clothing are available but not always used to maximum efficiency. Dose awareness and appropriate protection in response hereto are important issues for the Cathlab personnel as they spend many days per year in an environment exposing them to scattered radiation.

Scattered radiation is emitted from the body of the patient with energies that are most likely absorbed by the ambience, for example in the bodies of the medical staff. The spatial distribution of such scattered radiation is strongly dependent on the X-ray collimation, the patient geometry, and the used X-ray tube voltage. Such non-intuitive properties of the scattered radiation result in a difficult assessment of the risk for the personnel and, therefore, can result in an inappropriate dose protection equipment, imager settings, and protective clothing.

Generally, scattered radiation can be predicted by a scatter prediction device or can be measured by an appropriate radiation measuring device. Measured scattered radiation, e.g. determined by sensors worn by the personnel or installed in the room, can be combined with a prediction algorithm, leading to more accurate predictions of the scatter distribution.

Consequently, the ambient feedback indicating the scattered radiation can be based on both, predicted and sensed radiation (by detectors in the room or worn by personnel) or alternatively by either of them.

The density of predicted and/or measured scattered radiation, e.g. scattered x-ray, is transformed into perceptible signals indicative of the scattered radiation. For example, the density of scattered radiation in the room can be transformed into a floor plan that identifies different risk areas. The transformation into a floor plan can even be provided individually by taking into account information on the body size, weight, and sex of personnel in order to perform the transformation from the predicted or measured volume distribution of x-ray to a floor distribution of exposure risks.

Providing a perceptible signal indicative of the spatial distribution of scattered radiation, e.g. ambient feedback on the scatter distribution, is possible both before the actual irradiation (based on prediction) and during the irradiation (based on prediction, based on prediction and sensed radiation in combination, or based on sensed radiation) and can be updated live.

Scatter distributions cannot only be predicted for static geometries, but also for scenarios with temporally changing positions of the patient and/or the imaging device (e.g., 3D rotational angiography scans), which follow automatic, predefined protocols and include repeated or continuous radiation of the patient. Feedback on the integrated spatial scatter distribution generated by the whole procedure can then be made available to the personnel beforehand in order to e.g. suggest optimal positions during the automated scanning procedure, or at least emphasize the necessity to leave the room entirely during such procedures. Based on the predicted spatial distribution of a temporarily varying scattered radiation, an integrated spatial distribution of scattered radiation may be predicted. For example, a driving program of a spatially varying source of radiation, e.g. an X-ray source, may be taken into account for predicting an integral spatial distribution of radiation. In the following, the term "predicted spatial distribution of scattered radiation" includes both, an actual spatial distribution of scattered radiation as well as an integrated spatial distribution of scattered radiation.

FIG. 1 shows an exemplary embodiment of an imaging apparatus which involves the irradiation of an object with X-rays. In particular, FIG. 1 is a top view of technical equipment, in particular of an imaging apparatus, of an intervention room 1, e.g. a Cathlab, and further shows elements of embodiments of the invention. The imaging apparatus comprises a radiation source 2 which faces an diametrically opposed detector 4. The radiation source 2 and the detector 4 of the imaging apparatus are mounted on a support arm 6. The support arm 6 is rotatably mounted on a support 8 and is rotatable about an axis of rotation 10. A table 12 is provided for supporting an object 7, i.e. in the present embodiment a patient to be investigated. An X-ray image of the patient is generated from the X-rays received by the detector 4. The investigation image 9 which is processed by a workstation 11 can be viewed on a display device 13.

In order to facilitate the assessment of the distribution of scattered radiation, according to an embodiment of the invention it is proposed to predict a distribution of scattered radiation to the Cathlab personnel. The predictions may be showed in a way to indicate the radiation risk of scattered radiation in different areas of the intervention room 1 and, therefore, can lead to an informed decision of the personnel to use individually adapted dose protection and stay within uncritical areas of the room. Preferably, the prediction takes into account at least one object related parameter which is related to an object 7 that is subjected to a radiation and at least one radiation related parameter which is related to the radiation. In FIG. 1, the object 7 is a patient and the radiation is X-ray radiation. From these input parameters, a spatial distribution of scattered radiation is predicted, which would be generated by scattering of the radiation in a surrounding of the object 7, by taking into account the at least one object related parameter and the at least one radiation related parameter. Such a prediction can be carried out in a prediction unit 14 of a scatter prediction device 16. In the embodiment of FIG. 1, the prediction unit 14 is exemplarily implemented in the workstation 11, e.g. in an interventional workstation, of the imaging apparatus, e.g. by an appropriate computer program product, e.g. by an appropriate software module.

In the proposed embodiment shown in FIG. 1, at least one of patient sex, patient weight, patient size and patient age, is used as object related parameter 18 to configure a patient avatar, i.e. an algorithmic representation of the human body. Further, the chosen application package (e.g. cardio or neuro) which indicates which part of the body is target to x-ray imaging, may be used as an object related parameter 18. For inputting these object related parameters 18 and/or radiation related parameters into the prediction unit 14, an input device 20, e.g. a keyboard, is provided. However, any other method of inputting the parameters may be suitable, e.g. choosing predefined parameters with a selection device, e.g. a touch screen or a computer mouse. Such information may already be available as patient data, e.g. in the hospital's information system, such that the prediction unit could receive them without any user interaction. The configured patient avatar should provide an estimation on the distribution of x-ray exposed scattering matter.

As radiation related parameters, one or more of the following radiation related parameters can be input to the prediction unit 14:
 the position of the patient table
 the geometry of an imaging apparatus, in particular the distance between the source 2 and the object 7 or the distance between the source and the detector 4 as well as the position or orientation of source 2 and detector 4 in respect to object 7
 tube settings of the source 2
 filter settings for different modes of operation of the source 2
 shutter placement of the source 2 defining the radiated volume
 wedge placement; the wedge is e.g. provided for compensating different object thicknesses in the illuminated object range The radiation related parameters, indicated at 22 in FIG. 1, may be read out from the respective adjustment devices (not shown). Further, respective detecting devices may be provided. For example in the present embodiment, the table position 24 is provided by a table position detecting device 26.

The prediction can be implemented as simulation of the imaging process when the scattering matter estimated by the patient avatar is exposed to radiation in a field defined by imager geometry and shutters with an intensity and energy distribution defined by tube settings, wedges, and filters. Monte-Carlo simulations can provide a detailed prediction that can take into account all possible x-ray interactions with geometries of arbitrary detail level. Since such simulations require a lot of computing time, according to another embodiment it is proposed to create the prediction as superposition of pre-computed Monte-Carlo results. Pre-computed Monte-Carlo results may be obtained from lump models like water ellipses and other base elements. To this end, the prediction device may comprise a storage device for storing pre-computed Monte-Carlo results. The parameters of the patient model can be updated/optimized using the actually acquired images of the irradiated regions of the patient.

The prediction result may be the spatial distribution of scattered radiation or a spatial distribution indicative thereof. In an exemplary embodiment, the prediction result includes direction, intensity and energy distribution of scattered radiation in the air volume of the intervention room 1.

The scatter prediction device 16 may be operated for predicting a spatial distribution of scattered radiation in a surrounding of the object 7 by taking into account at least one object related parameter and at least on radiation related parameter, e.g. as described above. Further, one or more radiation measuring devices 25 may be provided which are fixedly installed as shown in FIG. 1. Alternatively, a radiation measuring device may be e.g. worn by personnel. The radiation measuring devices 25 may serve to improve the prediction of the scatter prediction device 16. For example, the measuring devices 25 may provide respective signals indicative of the measured scattered radiation to the prediction unit 14 which can verify the predictions at least for the positions of the radiation measuring devices 25.

In an alternative embodiment of the invention, the radiation measuring devices 25 may serve for predicting the spatial distribution of scattered radiation. In this embodiment, the radiation measuring devices measure the dose rate of scattered radiation at predetermined locations and the prediction device 16 may predict the spatial distribution of scattered radiation on the basis of these measurements, e.g. by interpolation.

According to still another embodiment of the invention, the scatter prediction may be refined by taking into account the acquired X-ray image information, i.e. the X-ray radiation detected by the detector 4, similar to the refinement by taking into account the signals of the measuring devices 25. For example, the prediction unit 14 may be adapted to predict a distribution of scattered radiation by taking into account the detector signals of the X-ray detector 4.

In response to the predicted spatial distribution of scattered radiation 27, the scatter prediction device 16 provides at least one perceptible signal 34. The at least one perceptible signal 34 is indicative of the predicted spatial distribution of scattered radiation 27. To this end, the scatter prediction device 16 may comprise a signalling system 28. A control unit 30 of the signalling system 28 provides control signals 29 in response to the predicted spatial distribution of scattered radiation 27. A signalling unit 32 provides at least one perceptible signal 34 in response to the control signals 29, the at least one perceptible signal 34 being indicative of the predicted spatial distribution of predicted scattered radiation 27.

Different visualizations and update strategies are proposed to beneficially provide this information to personnel which operates the imaging device or to personnel which carries out investigations under use of the imaging device, e.g. to Cathlab personnel. In order to assess and provide feedback on the individual risk of personnel given its sensed position, adequate models not only of the patient, but also of the personnel can be used. The models for the personnel are to be based on their characteristics (height, weight, sex, etc.) and their worn dose protection devices. The former can e.g. be stored in a database of the hospital's information system, for the latter, typical configurations can be used as default. Additionally, an optional manual entry of updated information about worn dose protection can be supported. In a simple embodiment, the prediction can be provided on demand, i.e. when the respective function is started by interested personnel.

In a another embodiment, the prediction is always provided and updated live. This may be of advantage because the provided information is always up to date and reflects the changes of risk areas in the intervention room 1 when the imager geometry is changed. Even more important, a live update that visualizes the effects of shutter and wedge placement can give a strong motivation to use these already available tools for image quality improvement and dose reduction.

Both, on-demand and live predictions can be presented and visualized with different tools, some of which are discussed in the following as different embodiments of the signalling system 28. A scatter prediction device may comprise only one embodiment of the signalling system. Further, a scatter prediction device can employ two or more of the herein described embodiments of a signalling system, as is exemplarily shown in FIG. 1.

An embodiment of a signalling system 28 is shown in FIG. 1. In this embodiment, at least one of the at least one perceptible signal 34 is a light pattern 36 on a floor 38 and the signalling unit 28 comprises at least one light source 40 for emitting light 41 for generating the light pattern 36. The light source 40 may be provided at the floor 38, beneath a surface 42 of the floor 38, on the surface 42 of the floor 38, or e.g. forming a surface of the floor 38. The light pattern 36 may form a floor plan indicating the spatial distribution of scattered radiation 27. Generating the light pattern 36 includes illuminating portions 44 of the floor 38, the portions 44 being vertical projections of spatial regions in which the radiation intensity, e.g. a radiation dose rate, exceeds a predetermined value, or lies within a predetermined intensity interval. According to one embodiment, one predetermined value of radiation intensity is provided. According to another embodiment, two or more predetermined values of radiation intensity are provided.

Further, as shown in the embodiment of FIG. 1, there may be provided at least one intensity interval, wherein providing the perceptible signal 34 includes illuminating portions 46 of the floor 38, the portions 46 being vertical projections of boundaries of spatial regions in which the radiation intensity is within one of the at least one, e.g. two ore more, predetermined radiation intensity intervals. The illuminated portions 46 generate iso-risk lines on the floor 38 like height lines known from cartographic maps.

Further, as shown in the embodiment of FIG. 1, there may be at least one radiation intensity interval, wherein providing the perceptible signal includes illuminating portions 48 of the floor, the portions 48 being projections of spatial regions in which the radiation intensity is within a predetermined radiation intensity interval and a specific color is associated with each of the radiation intensity intervals and wherein each of the illuminated portions 48 is illuminated with an illumination color corresponding to the respective radiation intensity interval.

It should be noted that the lines 46 and the regions 44, 48 on the floor of the embodiment of FIG. 1 are shown for illustrative purposes only and may extend around the table 12 or may exhibit a completely different pattern depending on the predicted spatial distribution of scattered radiation.

The light patterns on the floor may be generated in various different ways with various different embodiments of signaling units 32. In one embodiment, modules and methods from ambient lighting are used to project areas with different expected dose levels onto the floor of the Cathlab as an obvious visualization of the risk of irradiation by scattered x-ray that varies strongly in the room and depends on all imaging and patient characteristics. Such an embodiment is shown in FIG. 1 where the light pattern on the floor is provided by a signaling unit 32 comprising an ambient lighting module like an image projector. Further, signaling units comprising illumination lasers with pattern optics may be used to generate the desired light pattern. The image projector and the illumination laser may be used to project risk areas directly onto the floor in e.g. the Cathlab. E.g., iso-risk boundaries can be projected like height lines known from geographic maps. Colors and light intensity are further available as visualization tools, either in the form of floor projections or via individually illuminated floor panels.

Figure 3:
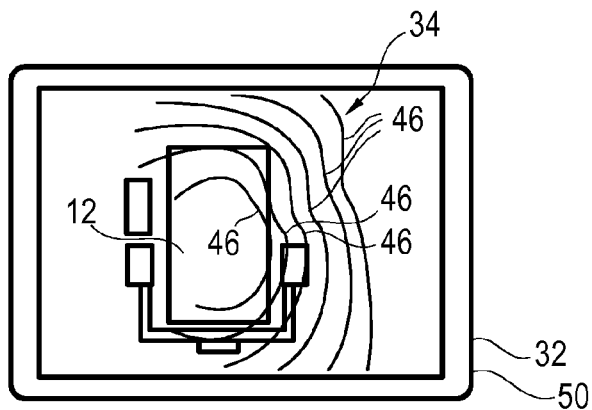
FIG. 3 shows in part an embodiment of a signalling system according to the invention.

FIG. 3 shows another embodiment of a signaling unit 32 in the form of a display device 50. The display device may be the display device 13 on which the investigation image of a patient is shown, or may e.g. a separate display device. A display device 13, 50 as signaling unit has the advantage that a floor pattern can be easily shown and does not require installations in the floor or on the ceiling of the room.

For visualization of the perceptible, visible signals 34, a realistic 3D rendering of the intervention room 1 with simulated rays and a floor plan of dose levels can be provided (not shown). A 3D rendering of the intervention room 1 with the imager in respective geometry and the patient avatar on the table can be used. In one embodiment of making the perceptible signals 34 visible in a display device 50, scattered x-rays are represented by pencil beams (i.e. lines in the rendering) with at least one of different intensity, different color, different density.

Figure 4:
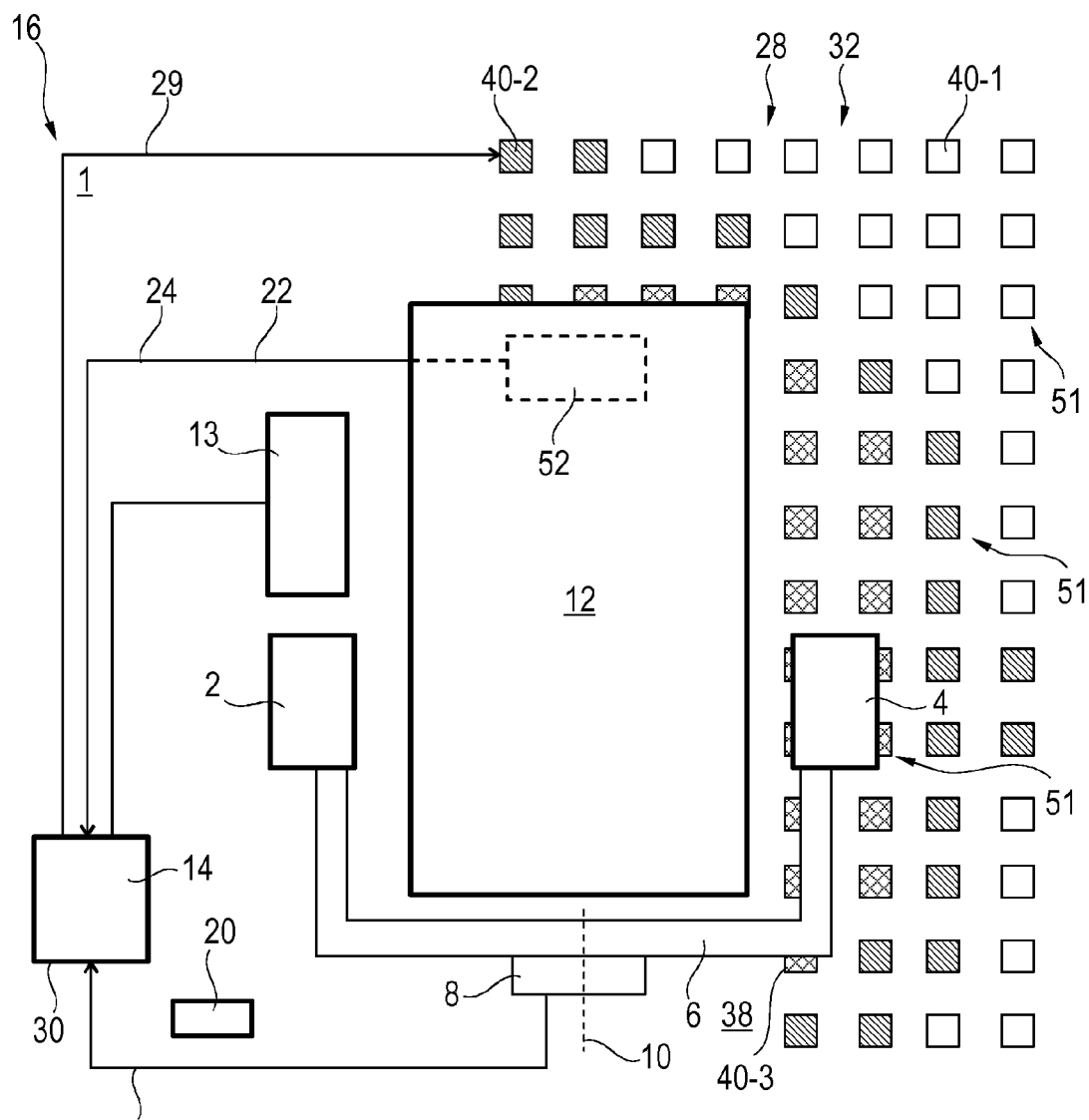
FIG. 4 shows a schematic top view of another embodiment of a scatter prediction device according to the invention.

FIG. 4 shows another embodiment of a scatter prediction device 16. Features and elements of the embodiment of FIG. 4 which have already been discussed with regard to FIG. 1 and which are indicated at the same reference numbers, are not repeated. Rather, reference is made to the details presented with regard to FIG. 1.

FIG. 4 shows another exemplary embodiment of a signaling unit 32 comprising a plurality of light sources 40 for generating the light pattern 36 on the floor 38. The light sources 40 are provided beneath a respective surface portion 42 of the floor 38. The surface portion 42 is formed by a wear protection that is transparent for the light of the light source. Any other position of the light sources 40 at the floor is also possible, as long as light of the light sources is perceptible for the personnel. The light sources 40 may comprise a flat light emitting element.

There may be provided at least one radiation intensity interval, wherein providing the perceptible signal includes illuminating portions 51 of the floor 38, the portions being projections of spatial regions in which the radiation intensity is within a predetermined radiation intensity interval and a specific illumination intensity is associated with each of the radiation intensity intervals and wherein each of the illuminated portions 51 is illuminated with an illumination intensity corresponding to its respective radiation intensity interval.

In the example shown in the illustrated embodiment, the light sources 40-1 which are depicted in white indicate low scatter exposure, the light sources 40-2 which are shaded indicate a medium scatter exposure and the light sources 40-3 which are depicted as solid indicate high scatter exposure. The depicted risks, in this embodiment low, medium and high scatter exposure, are presented only for illustrative purposes. It should be noted that part of the floor 38 of the intervention room 1, as shown in FIG. 4, or the whole floor of the intervention room 1 may be provided with the light sources 40.

In the embodiment shown in FIG. 4, the prediction unit 14 of the scatter prediction device 16 and the control unit 30 of the signalling system 28 are formed by a single device, e.g. a workstation. Further in this embodiment, the table position 24 is provided by an actual setting of a moving unit 52, which is provided for moving the table 12 up and down.

Figure 5:
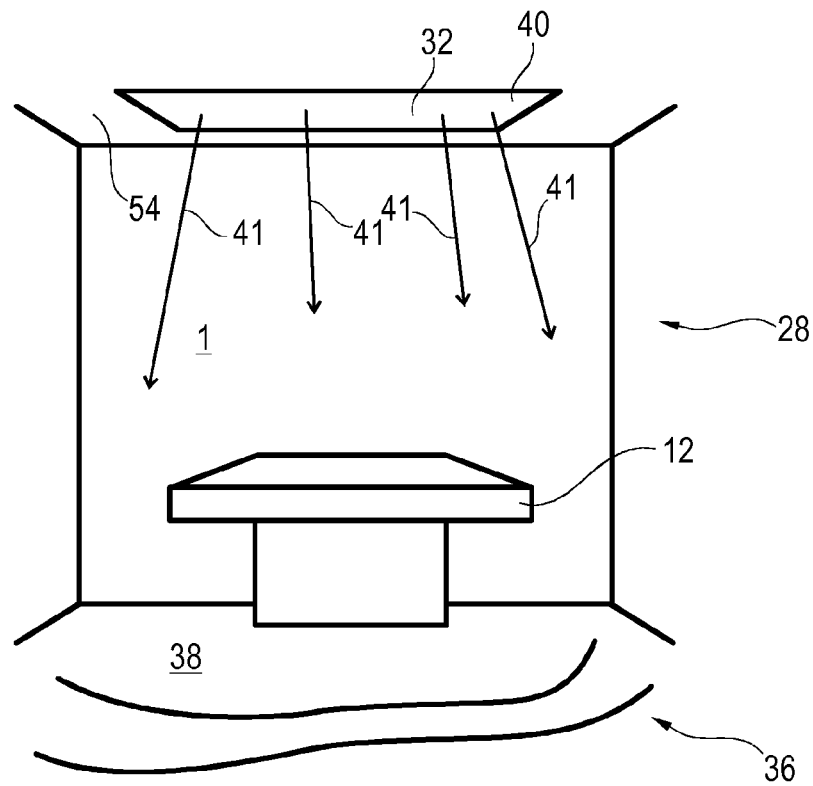
FIG. 5 shows in part a perspective view of another embodiment of a signalling system according to the invention.

FIG. 5 shows a perspective schematic view of an embodiment of an intervention room 1 with a table 12. Further technical equipment is not shown in FIG. 5 for the sake of clarity. At a ceiling 54 of the intervention room, a light source 40 for emitting light 41 is mounted for projecting the light pattern 36 onto the floor 38. In the illustrated embodiment, the light source 40 comprises a plurality of light source elements (not shown) each of which is capable of projecting a light dot onto the floor 38 in order to form the light pattern 36 on the floor 38.

Figure 6:
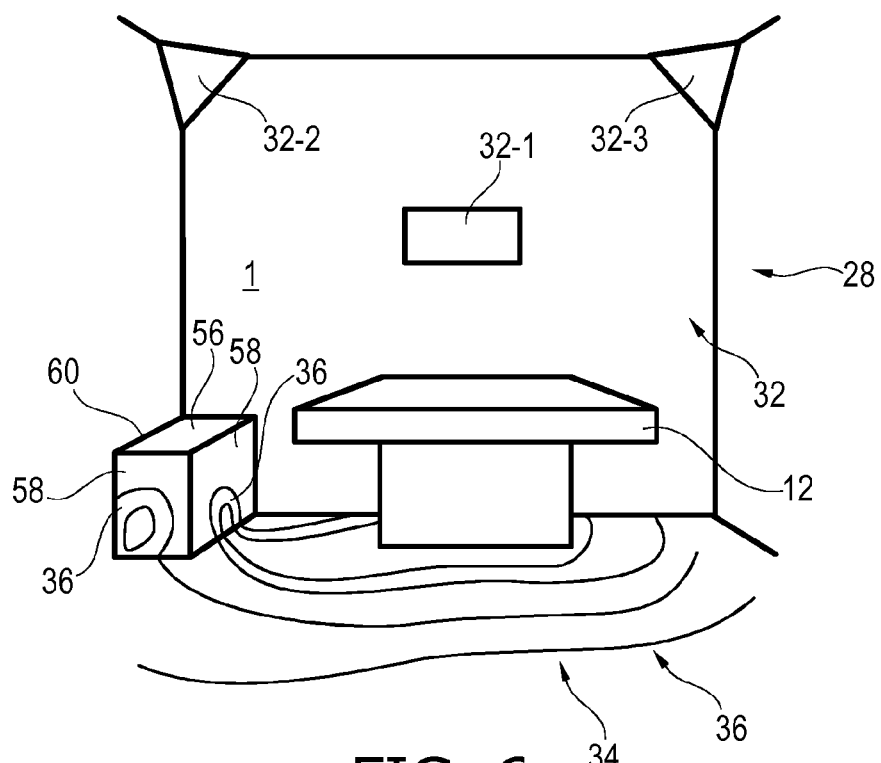
FIG. 6 shows in part a perspective view of still another embodiment of a signalling system according to the invention.

FIG. 6 shows a perspective schematic view of an embodiment of an intervention room 1 with a table 12. Representative for technical equipment in the intervention room 1, one piece of technical equipment 56 is shown in FIG. 6. A signalling unit 32 comprises elements 32-1, 32-2, and 32-3 which are positioned to produce the at least one perceptible signal 34 in the form of a light pattern 36 on a surface 58 of objects 60. Such objects 60 may include technical equipment 56 and the floor 38. Further, such objects 60 onto which a light pattern 36 is projected may include the patient itself. Instead of the elements 32-1, 32-2, or 32-3, any other configuration of the signalling unit 32 which can produce a light pattern on the desired surfaces of the desired objects is possible. For example, the signalling unit 32 of the embodiment shown in FIG. 1 may also be used for generating a light pattern on a surface of an object 60. The elements 32-1, 32-2, or 32-3 may be light sources, projectors, or any other suitable device.

In another embodiment of the present invention, a perceptible signal, e.g. an acoustic warning tone or a visible signal is generated if personnel enters floor regions where the personnel is exposed or where the personnel will be exposed to a certain X-ray dose from scattered radiation. To this end, an arbitrary position sensor may be provided in order to detect a position of medical personnel. The position sensor would be adapted to transmit a signal indicative of the position of the personnel to the control unit 30. Alternatively or additionally, the personnel may wear a radiation sensor for sensing radiation indicative of the scattered radiation at the location of the radiation sensor. For example, the radiation indicative of the scattered radiation may be the scattered radiation itself, i.e. the radiation sensor may be an X-ray sensor. The radiation sensor is adapted to transmit a signal indicative of the scattered radiation to the control unit 30. Transmitting a signal to the control unit 30 includes transmitting the signal to the control unit 30 by wire. Alternatively, transmitting a signal to the control unit includes transmitting the signal to the control unit 30 by a wireless technique, a plurality of which is known in the art. The radiation sensor indicative of the scattered radiation at the location of measurement can be placed at an arbitrary position of the personnel. In particular the radiation sensor may be positioned near sensitive portions of a body of the personnel, e.g. near a loin or a thorax.

Figure 7:
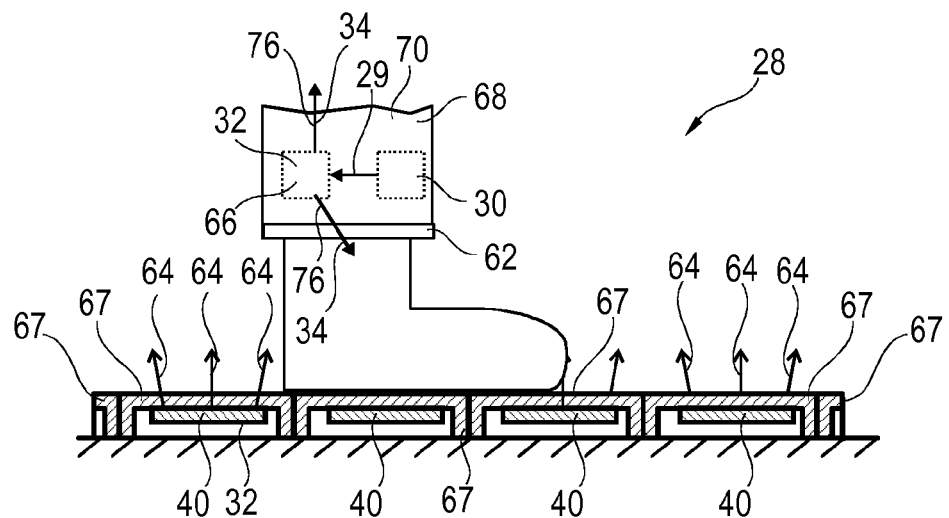
FIG. 7 shows in part a cross-sectional view of still another embodiment of a signalling system according to the invention.

FIG. 7 shows a further embodiment of a signalling system 28. The signalling system 28 of this illustrated embodiment comprises a radiation sensor 62 for sensing radiation 64 indicative of the predicted spatial distribution of scattered radiation at the position of the radiation sensor; and an acoustic signalling device 66 as signalling unit 32. Light sources 40, which generate the radiation 64 indicative of the predicted spatial distribution of scattered radiation, may be themselves parts of a signalling unit of a signalling system according any of the aspects and embodiments of invention disclosed herein. The light sources 40 may be e.g. the light sources 40 of the embodiment depicted in FIG. 4. In the illustrated embodiment, each of the light sources 40 is covered by a wear protection 67, e.g. a tile of transparent material, e.g. glass. The acoustic signalling device 66 may comprise e.g. a loudspeaker for generating acoustic signals 76. The control unit 30 of the signalling system 28 provides the control signals 29 to the acoustic signalling device 66 in response to the sensed radiation 64. The acoustic signalling device 66 generates perceptible signals 34 in the form of acoustic signals 76 in response to the control signal 29.

In the illustrated embodiment of FIG. 7, the signalling system 28 is a wearable acoustic signalling system, which can be positioned e.g. on cloth of the personnel of an X-ray imaging apparatus. In FIG. 7, the signalling system 28 is positioned in one leg 68 of a pair of trousers 70. Alternatively, each leg of the pair of trousers may comprise a signalling system 28. The illustrated embodiment shall not be considered as limiting. Many other possible applications of acoustic signalling systems are possible.

Figure 8:
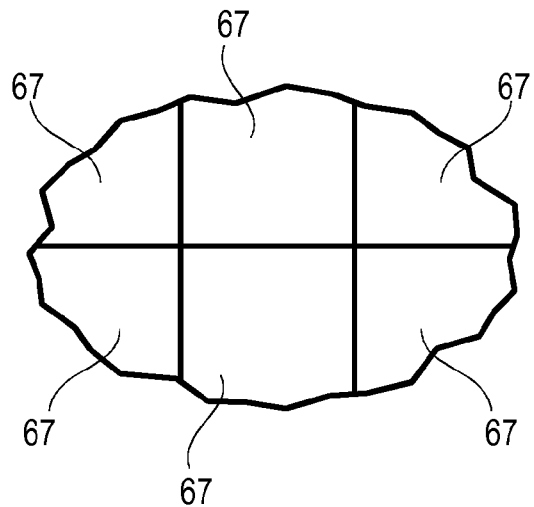
FIG. 8 shows a top view of the signalling system of FIG. 7.

FIG. 8 shows a partial top view of the surface which is established by the wear protections 67.

Figure 9:
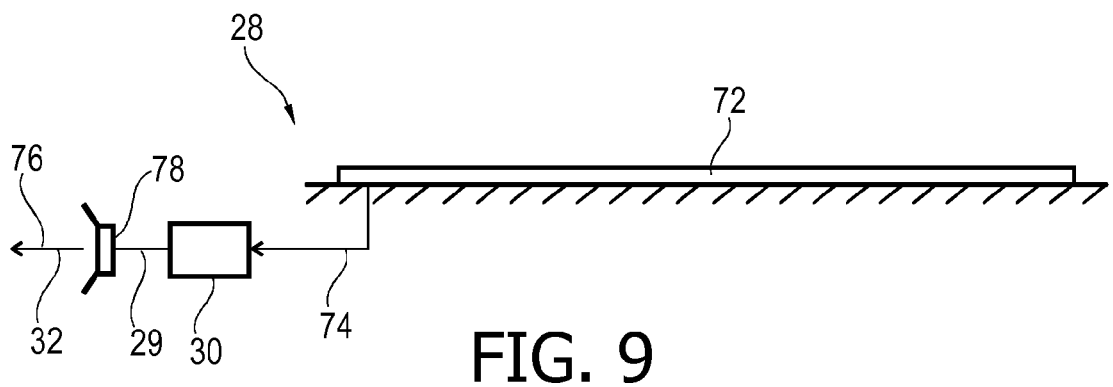
FIG. 9 shows in part a cross-sectional view of still another embodiment of a signalling system according to the invention.

FIG. 9 shows a further embodiment of a signalling system 28 providing a perceptible acoustic signal. The signalling system 28 of this illustrated embodiment comprises a sensing device 72 for sensing a position of an individual and providing a position signal 74 to the control unit 30 of the signalling system 28 in response hereto. The sensing device 72 may comprise e.g. a pressure sensitive element, an optical sensor or an ultrasonic sensor. In this embodiment, at least one of the at least on perceptible signal 34 is an acoustic signal 76 and the signalling unit 28 comprises at least one acoustic signal source 78 for providing the acoustic signal 76 in response to control signals 29 of the control unit 30. The control unit 30 provides control signals 29 to the at least one acoustic signal source 78 in response to the predicted spatial distribution of scattered radiation and the position signal 74. The acoustic signal 34, 76 is indicative of the predicted spatial distribution of scattered radiation at the location of the sensing device 72.

Figure 10:
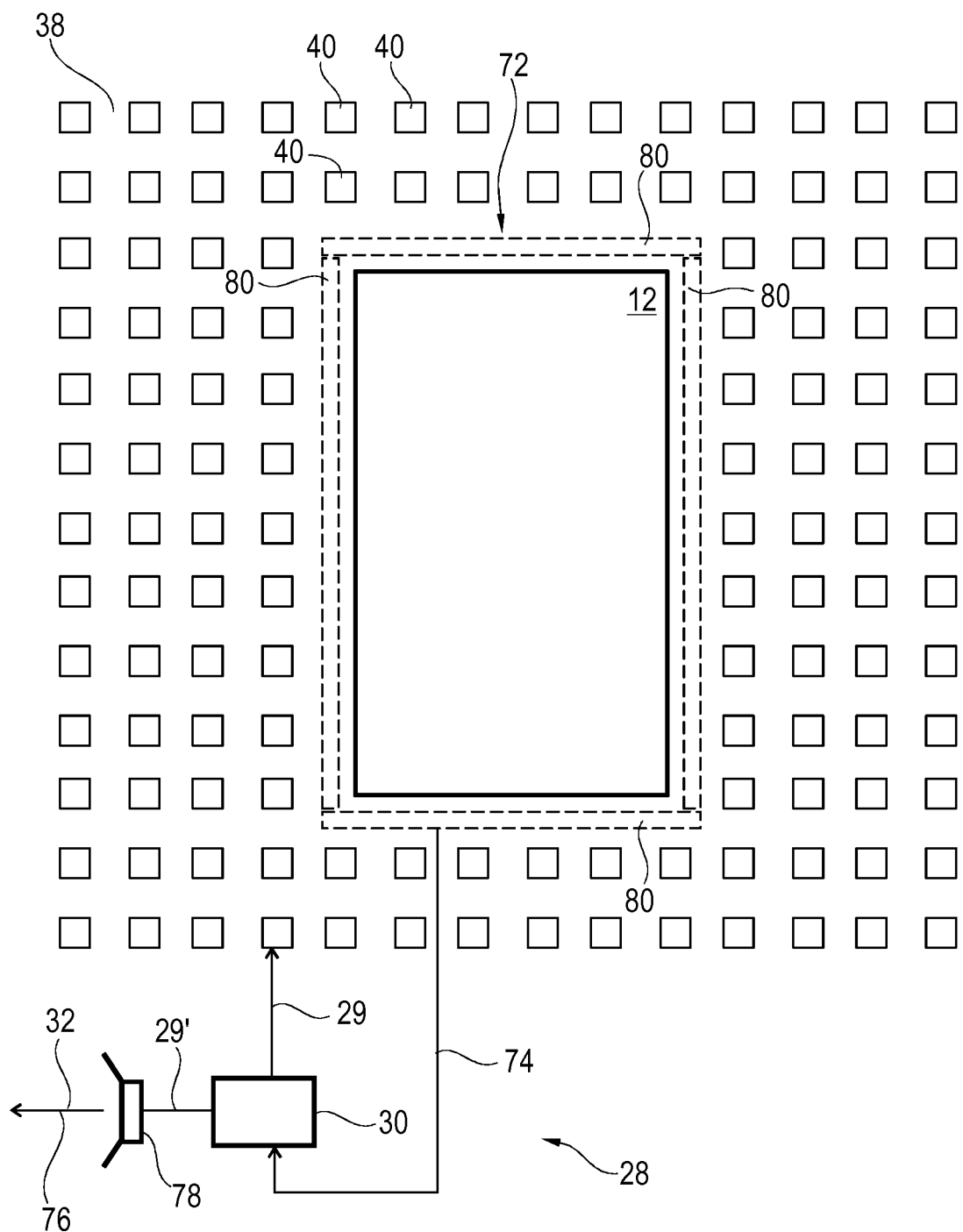
FIG. 10 shows a schematic top view of another embodiment of a scatter prediction device according to the invention.

FIG. 10 shows another embodiment of a signalling system 28 providing a perceptible acoustic signal. Technical equipment like the imaging device comprising source 2 and detector 4 is not shown in FIG. 10. The signalling system comprises a plurality of light sources 40, similar to the light sources depicted in FIG. 4. In the embodiment of FIG. 10 the light sources 40 are provided over the whole area of the floor 38. The control unit 30 provides control signals (represented at 29 in FIG. 10) in response to a predicted spatial distribution of scattered radiation to the light sources 40 which in response hereto provide a perceptible signal 34 in the form of visible light. The signalling system 28 of this illustrated embodiment further comprises a sensing device 72 for sensing a position of an individual and providing a position signal 74 to the control unit 30 of the signalling system 28 in response hereto. The sensing device 72 in this embodiment comprises at least one light sensing element 80, e.g. four light sensing elements 80. The light sensing elements 80 receive the light emitted from the light sources 40. Depending on a position of an individual, at least one of the at least one light sensing elements 80 is shaded. In response to the shading, the position signal is generated by the sensing device 72.

The control unit 30 provides a control signal 29' to the at least one acoustic signal source 78 in response to the predicted spatial distribution of scattered radiation and the position signal 74. In response to the control signal 29', the at least one acoustic signal source 78 generates an acoustic signal 76. In this embodiment, one of the perceptible signals 34 is an the acoustic signal 76 and one of the perceptible signals 34 is the light emitted from the light sources 40 (not shown).

The control unit of the embodiments shown in FIG. 7, FIG. 8, FIG. 9 or FIG. 10 may be configured to provide control signals such that the acoustic signal source generates an acoustic signal of a tone pitch which is indicative of the predicted spatial distribution of scattered radiation. For example, personnel approaching a high risk zone can be acoustically warned by a rising tone pitch corresponding to a predicted higher dose rate.

Figure 11:
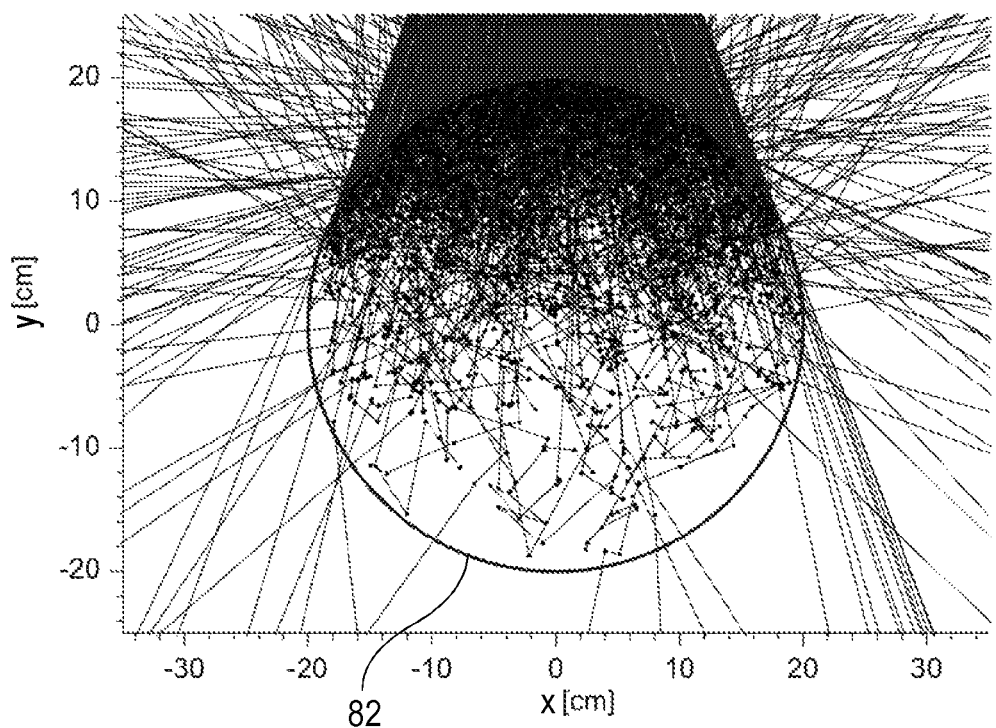
FIG. 11 shows a front view of an exemplary embodiment of an object exposed to radiation and the scattered radiation produced by the object.
Figure 12:
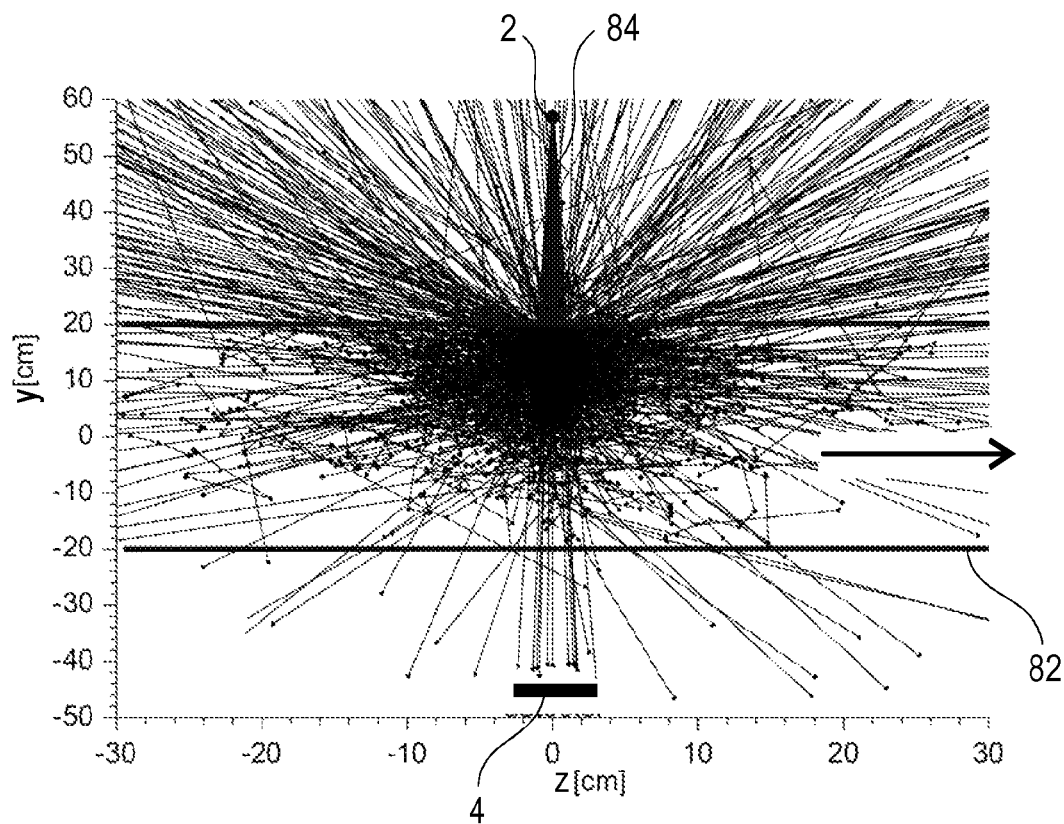
FIG. 12 shows a side view of the object of FIG. 10.

With regard to FIG. 1, an embodiment of a prediction device and a prediction method for predicting a spatial distribution of scattered radiation has already been discussed. In the following, further embodiments of a prediction device 16 or a prediction method are presented which can be used to advantage of more refined algorithmic representation of the object 7. Regarding the prediction of the spatial distribution of scattered radiation, an example of scattering arising from an irradiated phantom is shown in FIGS. 11 and 12, which provides a visualization of scatter radiation emitted from a very simple patient model, a 40 cm water cylinder 82. FIG. 11 shows a front view and FIG. 12 shows a side view of the water cylinder 82. In FIG. 11, lines represent photon trajectories and dots represent direction changes of photons due to scatter. The illumination corresponds to a fan beam 84 which is provided by a source 2. The fan beam 84 covers the whole cross-section of the cylinder 28. A detector 4 is placed diametrically opposed the source 2.

Figure 13:
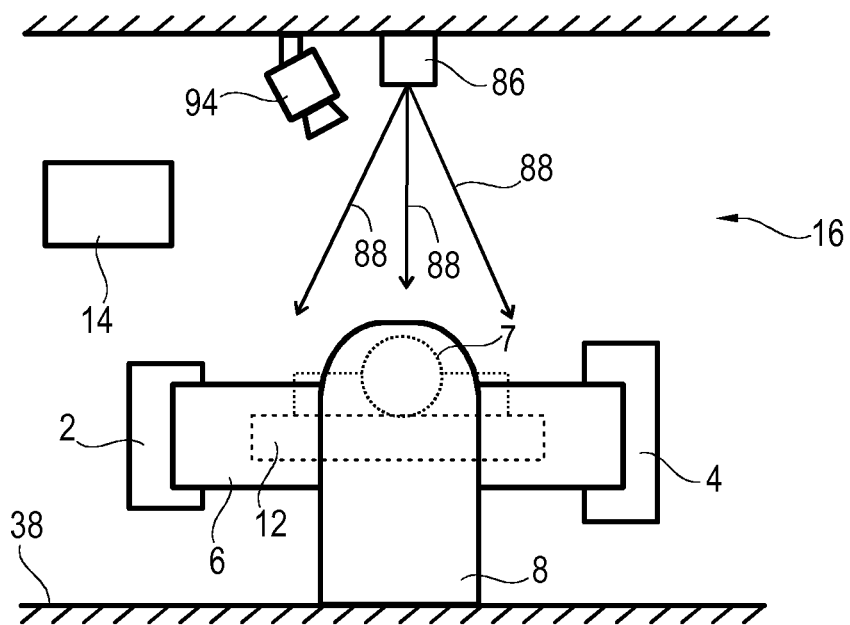
FIG. 13 shows a front view of still another embodiment of a scatter prediction device according to the invention.
Figure 14:
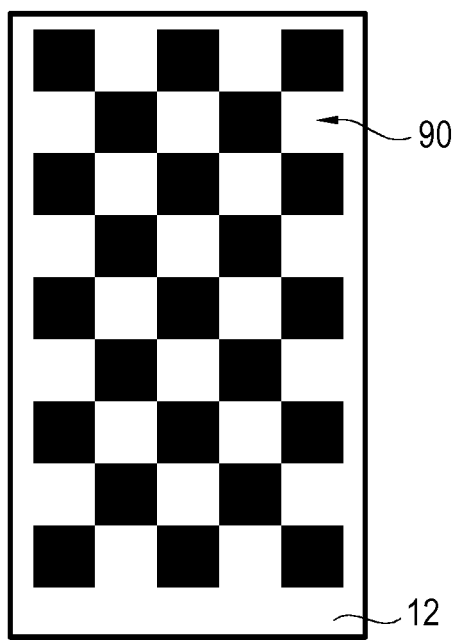
FIG. 14 shows a light pattern produced by still another embodiment of a scatter prediction device according to the invention.
Figure 15:
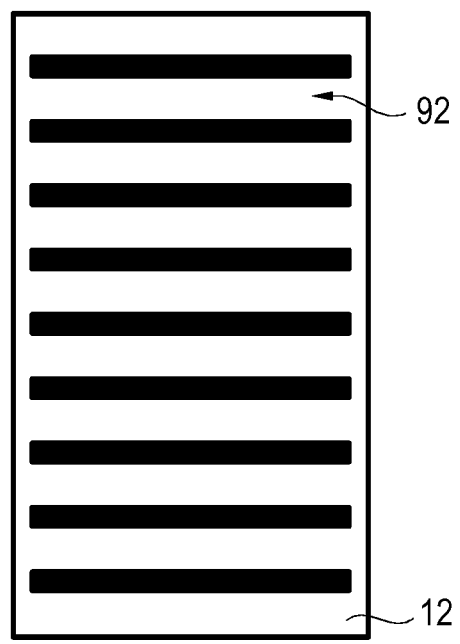
FIG. 15 shows a light pattern produced by still another embodiment of a scatter prediction device according to the invention.

In an embodiment, detailed geometric information about the patient shape is obtained via an optical scan using structured light on the patient and detecting the distortion of the projected pattern. FIG. 13 shows an example of a prediction device 16 which is suitable for this purpose. The prediction device comprises a light source 86 for projecting structured light 88 onto the object 7, i.e. onto the patient in the illustrative embodiment thereby generating an light pattern on the object 7. FIG. 14 shows an exemplary embodiment of a projected light pattern, a checkerboard light pattern 90, on the empty table 12. FIG. 15 shows another exemplary embodiment of a projected light pattern, a stripe light pattern 92, on the empty table 12. The projected light pattern 90, 92, which is distorted by the object 7, is scanned with a scan device 94, e.g. a camera. From the scanned distorted pattern, a prediction unit 14 calculates at least one object related parameter, e.g. at least one of an object thickness, object shape, object mass, etc.

In another refined embodiment, at least one of the algorithmic representation of the object, e.g. the patient avatar, and imaging configuration of the prediction is modified in response to already acquired x-ray images of the same object. Further, at least one of the algorithmic representation of the object, e.g. the patient avatar, and an imaging configuration of the prediction is modified in response to already performed predictions of spatial distributions of scattered radiation. "Modifying" in this sense includes fine-tuning of the algorithmic representation of the object and the imaging configuration, respectively.

Figure 16:
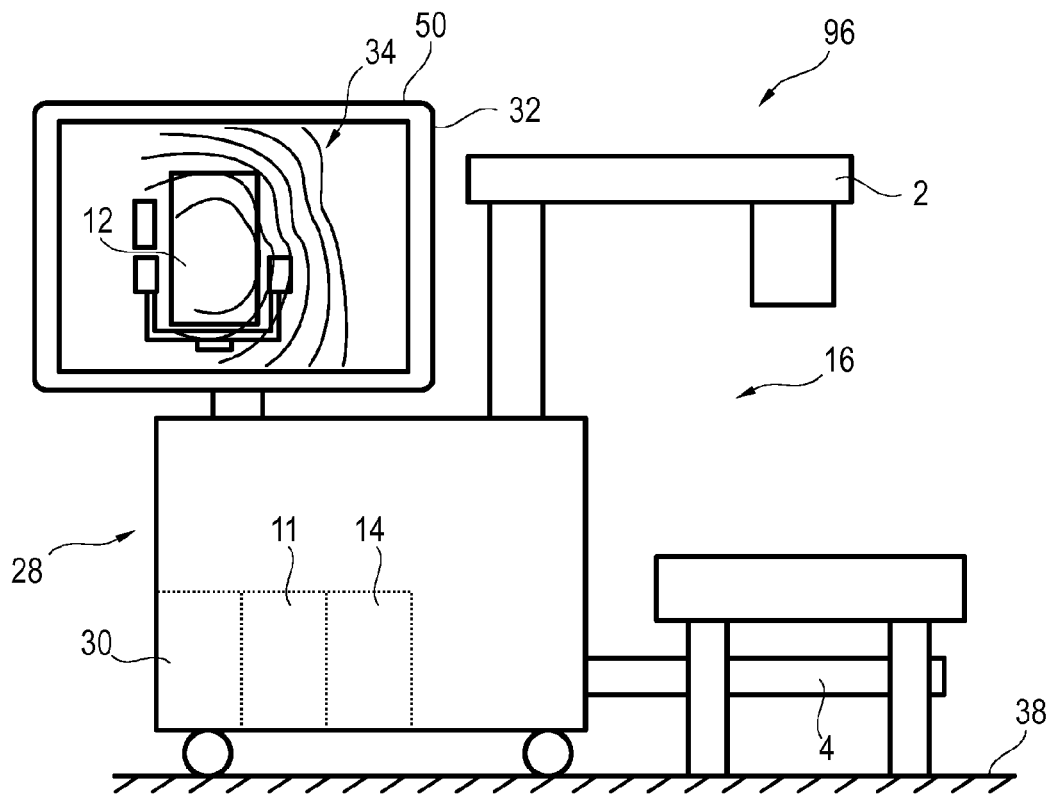
FIG. 16 shows a side view of still another embodiment of a scatter prediction device according to the invention.

FIG. 16 shows a mobile X-ray examination device 96 comprising a signalling system 28 comprising a control unit 30 for providing control signals 29 in response to a predicted spatial distribution of scattered radiation, and a signalling unit 32 for providing at least one perceptible signal in response to the control signals, the at least one perceptible signal being indicative of the predicted spatial distribution of scattered radiation. Alternatively, the mobile X-ray examination device 96 may comprise a control unit 30 for providing control signals in response to a measured spatial distribution of radiation, as illustrated herein. Alternatively, the mobile X-ray examination device 96 may comprise a control unit 30 for providing control signals in response to a predicted and a measured spatial distribution of radiation, as illustrated herein. A suitable embodiment of a signalling unit is a display device, e.g. a display device as described with regard to FIG. 3. However other embodiments of signalling units as described above may be implemented in a mobile X-ray examination device, e.g. signalling units comprising a light source 40 for projecting a pattern indicative of the spatial distribution of scattered radiation onto a floor 38 (not shown). Further, the mobile X-ray examination device may comprise a scatter prediction device 16 having a prediction unit 14. Details about features which have been discussed with regard to other embodiments and which are indicated at the same reference signs, are not repeated. Rather reference is made to the other embodiments. Other features of any of the above embodiments may be included in a mobile X-ray examination device if technically possible.

Figure 17:
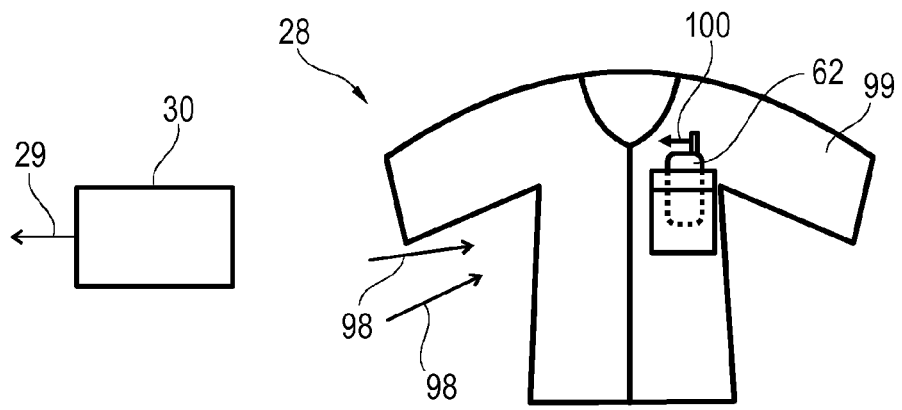
FIG. 17 shows a partial side view of still another embodiment of a signalling system according to the invention.

FIG. 17 shows a part of a further embodiment of a signalling system 28 comprising a control unit 30 for providing control signals 29 in response to a measured spatial distribution of scattered radiation. A signalling unit for providing at least one perceptible signal in response to the control signals 29 is not shown in FIG. 17, but may be designed in any appropriate way, e.g. according to any embodiment of a signalling unit disclosed herein. The signalling system 28 further comprises a radiation sensor 62 for sensing a radiation indicative of a spatial distribution of scattered radiation. In particular the radiation sensor 62 of FIG. 17 is an X-ray radiation sensor for directly sensing scattered X-ray radiation 98. The control unit 30 provides the control signals 29 in response to the sensed radiation 98. In the embodiment shown in FIG. 17, the radiation sensor 62 is a mobile radiation sensor which may be positioned in a pocket of a shirt 99. Wireless signals, e.g. a radio signal 100 is emitted from the radiation sensor 62, the radio signal 100 being indicative of the sensed radiation 98. The radio signal 100 is received by the control unit 30 which in response hereto generates the control signals 29. It should be understood that radio signal 100 is only described for illustrative purposes and that any other suitable means, wired and wireless can be used for providing the control unit 30 with a signal indicative of the sensed radiation 98.

Summing up some embodiments, according to an embodiment of the invention, a valuable information for personnel is the scattered radiation intensity for different locations in the intervention room 1. The density of scattered x-ray in the room can be transformed into a floor plan that identifies different risk areas. This transformation can even be provided individually when information on the body size, weight, and sex of personnel is input to the transformation from the volume distribution of x-ray to a floor distribution of exposure risks. This map can be presented on Cathlab monitors as well.

In another embodiment, ambient lighting devices indicate an X-ray dose rate from scattered radiation on the surface of 3D objects which could be, e.g., technical equipment or clothes of the personnel.

In another embodiment of the present invention, an acoustic warning tone is generated if medical personnel enters floor regions where they are exposed or where they will be exposed to a certain X-ray dose from scattered radiation.

For example, the floor regions may be illuminated to indicate enhanced X-ray dose from scattered radiation and the personnel wears a signaling system which generates the acoustic warning tone. According to another embodiment, the certain floor regions may comprise at least one position sensor to detect the position of personnel. The acoustic tone may also indicate the amount of dose (e.g. by the pitch of the tone). To this end, light sensors may be carried by the personnel (then the tone is generated, when the light sensor detects light generated by the floor illumination source) or light sensors may be integrated into the floor around the intervention table (then the tone is generated, when the light from the floor illumination source is shadowed by the personnel entering the critical floor region), and the light sensors must be selectively sensitive to the light and color of the floor illumination source.

The invention is applicable to all environments in which personnel works in scattered radiation. In particular, the invention is applicable to all minimally-invasive interventions under x-ray guidance and surveillance. Exemplary embodiments are proposed for Cathlabs. The invention can be installed as additional feature and extension package in all existing Cathlab intervention rooms or bundled with new installations. The computation of scattered radiation risk areas can be executed on interventional workstations linked to the Cathlab imager. The identified risk areas and expected dose levels of personnel exposure can be presented on a monitor on the respective stand in the intervention room 1 or used to control ambient lighting elements in the room that are able to project structured information onto the floor of the room.

Irrespective of how the perceptible signal being indicative of the predicted spatial distribution of scattered radiation is provided, the perceptible signal can give a direct feedback on the success of dose awareness steps like wedge and shutter placement, which is beneficial for both, image quality as well as patient and personnel exposure.

Especially the combination of the floor projections with a live update of the predictions (including acoustical warning) can be used to strongly improve dose awareness for personnel and, therefore, as motivation to use all available tools of dose protection. Dedicated Cathlabs equipped with this extra feature are further proposed as important tool for teaching of dose awareness.

While the invention has been illustrated and described in detail in the drawings and foregoing description, such illustration and description are to be considered illustrative or exemplary and not restrictive; the invention is not limited to the disclosed embodiments.

For example, the invention is not limited to the use of X-rays as radiation. Rather, the invention embraces other kinds of radiation. Accordingly, the illustrated embodiments may be realized with any other radiation that is suitable for the desired kind of investigation, e.g. neutron radiation.

Further, although in some drawings an example of an imager comprising a radiation source and a detector has been depicted for illustrative purposes, it should be understood that none of the above embodiments is limited to the depicted kind of imager. Rather any of the embodiments can be carried out with a configuration having a radiation source and an object 7 which is irradiated with the radiation. Moreover, if technically possible, any of the presented aspects and embodiments can be carried out with any configuration that generates scattered radiation.

Further, although the illustrated embodiments relate to embodiments which are intended for investigation of humans, it should be understood that the invention and the embodiments described therein can be employed in any other environment where personnel is working in scattered radiation. An example of such another environment is e.g. a scientific laboratory which uses an X-ray diffraction apparatus e.g. for the characterization of materials. In such an environment, the invention may be useful for the calibration of the X-ray diffraction apparatus which requires manual interaction.

Other variations to the discussed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. Further, generally a unit that performs more than one method can be represented by two respective units each of which performs one of the two or more methods. The mere fact that certain measures are recited in mutually different dependent claims does no indicate that a combination of these measures cannot be used to advantage. A computer program product may be provided for each embodiment of a method described in this patent application, wherein the computer program product enables a processor to carry out the respective embodiment of a method. A computer program may be stored/distributed on a suitable medium supplied together with or as part of other hardware, but may also be distributed in other forms, such as via the Internet or other wired or wireless telecommunication systems. Any reference signs in the claims should not be construed as limiting the scope.

The invention claimed is:

1. A signalling apparatus comprising:
    a prediction processor for generating a predicted spatial distribution of scattered radiation;
    a radiation sensing device for sensing radiation indicative of a measured spatial distribution of scattered radiation;
    a control unit for providing control signals in response to the predicted and/or the measured spatial distribution of scattered radiation;
    a signalling unit for providing at least one perceptible signal in response to said control signals, said at least one perceptible signal being indicative of the predicted and/or the measured spatial distribution of scattered radiation; and
    a position sensing device for sensing a position of an individual and providing a position signal to said control unit in response hereto.

2. The signalling apparatus according to claim 1, wherein at least one of said at least one perceptible signal is a light pattern on a floor or on a surface of at least one object; and said signalling unit comprises at least one light source for generating said light pattern.

3. The signalling apparatus according to claim 1, further comprising:
    an acoustic signal source for providing an acoustic signal in response to control signals of the control unit;
    wherein at least one of said at least one perceptible signal is an acoustic signal indicative of said spatial distribution of scattered radiation at the position of the individual;
    wherein said control unit provides said control signals to said acoustic signal source in response to said spatial distribution of scattered radiation and said position signal.

4. An intervention room for performing interventions under X-ray surveillance, said intervention room comprising the signalling apparatus according to claim 1.

5. A mobile X-ray examination device comprising a signalling apparatus according to claim 1.

6. The signalling apparatus according to claim 1, wherein the position sensing device senses the position of an individual and is located within the signalling apparatus or in a wearable signalling device worn by an individual.

7. The signalling apparatus according to claim 1, wherein the radiation sensing device senses X-ray radiation or visible light and is fixedly installed on an object or in a wearable radiation sensing device worn by an individual.

8. The signalling apparatus according to claim 2, wherein the light pattern has one or more color levels, or one or more light intensity levels, or one or more iso-risk lines, or one or more risk areas.

9. The signalling apparatus according to claim 2, further comprising a scan device for detecting a distorted structured projected light pattern, wherein the prediction processor determines at least one object related parameter using the distorted structured projected light pattern.

10. The signalling apparatus according to claim 9, wherein the prediction processor generates the predicted spatial distribution of scattered radiation using the at least one object related parameter and a superposition of pre-calculated Monte Carlo simulations.

11. The signalling apparatus according to claim 3, wherein the acoustic signal source is located within the signalling apparatus or in a wearable acoustic signal device worn by an individual.

12. The signalling apparatus according to claim 3, wherein the acoustic signal source emits a rising tone pitch corresponding to a higher radiation dose.

13. A method for signalling exposure to radiation, the method comprising:
    generating a predicted spatial distribution of scattered radiation;
    sensing radiation indicative of a measured spatial distribution of scattered radiation;
    sensing a position of an individual and providing a position signal;
    generating a control signal from the predicted and/or the measured spatial distribution of scattered radiation and the position signal;
    providing at least one perceptible signal in response to the control signal, the at least one perceptible signal being indicative of the predicted and/or the measured spatial distribution of scattered radiation or the position of the individual.

14. The method of claim 13, wherein at least one of said at least one perceptible signal is a light pattern on a floor or on a surface of at least one object.

15. The method of claim 13, wherein at least one of said at least one perceptible signal is an acoustic signal indicative of said spatial distribution of scattered radiation at the position of the individual.

16. The method according to claim 13, wherein the radiation sensing device senses X-ray radiation or visible light and is fixedly installed on an object or in a wearable radiation sensing device worn by an individual.

17. The method according to claim 14, wherein the light pattern has one or more color levels, or one or more light intensity levels, or one or more iso-risk lines, or one or more risk areas.

18. The method according to claim 14, wherein the light pattern is a structured projected light pattern, and further comprising using a scan device for detecting a distorted structured projected light pattern, and using the prediction processor for determining at least one object related parameter using the distorted structured projected light pattern.

19. The method according to claim 14, further comprising predicting the predicted spatial distribution of scattered radiation using the at least one object related parameter and a superposition of pre-calculated Monte Carlo simulations.

20. The method according to claim 14, further comprising using the acoustic signal source for emitting a rising tone pitch corresponding to a higher radiation dose.

21. A non-transitory computer-readable medium having stored thereon instructions for performing the steps of the method for signalling exposure to radiation according to claim 13.

\* \* \* \* \*